(12) United States Patent
Yang et al.

(10) Patent No.: US 8,377,276 B2
(45) Date of Patent: Feb. 19, 2013

(54) HIGH TEMPERATURE AND HIGH PRESSURE REFERENCE ELECTRODE AND METHOD TO ELIMINATE THE FORMATION OF GAS BUBBLES IN LIQUID-FILLED TUBES

(76) Inventors: Lietai Yang, San Antonio, TX (US);
Xiaodong Sun Yang, San Antonio, TX (US)

(*) Notice: Subject to any disclaimer, the term of this patent is extended or adjusted under 35 U.S.C. 154(b) by 1104 days.

(21) Appl. No.: 12/290,388

(22) Filed: Oct. 30, 2008

(65) Prior Publication Data
US 2010/0108511 A1 May 6, 2010

(51) Int. Cl.
*G01N 27/30* (2006.01)
(52) U.S. Cl. .................................. 204/435; 204/433
(58) Field of Classification Search .................. 204/435, 204/433, 416
See application file for complete search history.

(56) References Cited

U.S. PATENT DOCUMENTS

| 4,273,637 | A | | 6/1981 | MacDonald et al. | |
|---|---|---|---|---|---|
| 4,818,366 | A | * | 4/1989 | Yonco et al. | 204/408 |
| 5,516,413 | A | * | 5/1996 | Foster et al. | 204/435 |

OTHER PUBLICATIONS

D. D. Macdonald, "Reference Electrodes for High Temperature Aqueous Systems—A Review and Assessment," Corrosion, vol. 34, p. 76-84(1978).
A.K. Agrawal and R.W. Staele, "A Silver-Sivler Chloride Reference Electrode for the High Temperature and High Pressure Electrochemistry," Corrosion, vol. 33, p. 418-419(1977).
S. H. Oh, C.B. Bahn, and I. S. Hwang, "Evaluation of Thermal Liquid Junction Potential of Water-Filled External Ag/AgCl Reference Electrodes," Journal of the Electrochemical Society, 150 p. E321-E328 (2003).
C.M. Menendez, "Reference Electrodes for High Pressure and High Temperature Electrochemical Testing," CORROSION/2001, paper, 01305, (Houston, TX: NACE International, 2001)].

* cited by examiner

*Primary Examiner* — Kaj K Olsen

(57) ABSTRACT

A long-term, reliable high pressure reference electrode for high temperature applications was disclosed. This reference electrode has inner and an outer liquid junction plugs. The inner plug provides the function of restraining the outflow of the internal reference electrolyte. The outer plug is chemically and mechanically robust in the external fluid where the reference electrode is used and protects the inner plug from the mechanical and chemical attacks by the harsh external fluid. Therefore, the inner plug can be selected from many of the well-characterized liquid junction plugs used in regular low temperature reference electrodes, without the need for the inner plug to be chemically and mechanically stable in the external fluid, as long as it has the thermal stability.
A method for preventing the formation of gas bubbles inside a high pressure reference electrode in the electrolyte-filled section, and thus eliminating the gas bobble effect on the electrical continuity, was also disclosed. One or more thin solid rods or tubes are inserted into the internal electrolyte-housing tube and the thin rods or tubes alter the surface tension of the gas bubbles so that the bubbles are unstable in the middle of the liquid electrolyte. Compared with the fiber wicks or porous powder used by previous researchers to ensure the electrical continuity, the thin tubes or rods are easier to handle and easier to clean. This method may also be used in other systems that contain a liquid-filled tube (e.g., a pH electrode) to prevent the formation of gas bubbles in the liquid-filled section of the tube.

6 Claims, 5 Drawing Sheets

HIGH TEMPERATURE AND HIGH PRESSURE REFERENCE ELECTRODE AND METHOD TO ELIMINATE THE FORMATION OF GAS BUBBLES IN LIQUID-FILLED TUBES

TECHNICAL FIELD OF THE INVENTION

This invention relates to pressure balanced reference electrodes and pH electrodes for high pressure and/or high temperature applications.

BACKGROUND OF THE INVENTION

High pressure and high temperature reference electrodes are widely used for corrosion control and electrochemical studies [see D. D. Macdonald, "Reference Electrodes for High Temperature Aqueous Systems—A Review and Assessment," *Corrosion*, Vol. 34, page 76-84, 1978, and C. M. Menendez, "Reference Electrodes For High Pressure And High Temperature Electrochemical Testing," *CORROSION/2001*, paper, 01305, (Houston, Tex.: NACE International, 2001)]. This invention is related to the long-term reliable reference electrode and a method for eliminating the formation of gas bubbles inside a reference or a pH electrode tube filled with a liquid. Such gas bubbles formed inside the tube in the liquid section often affect the electrical continuity between the top and bottom ends of an electrode.

BRIEF DESCRIPTION OF THE DRAWINGS

FIG. 1 illustrates a typical tube type of high pressure reference electrode that has two liquid junction plugs and a sand powder section in between.

FIG. 2 illustrates a typical thread type of high pressure reference electrode that has two liquid junction plugs and a sand powder section in between.

Figure 1:
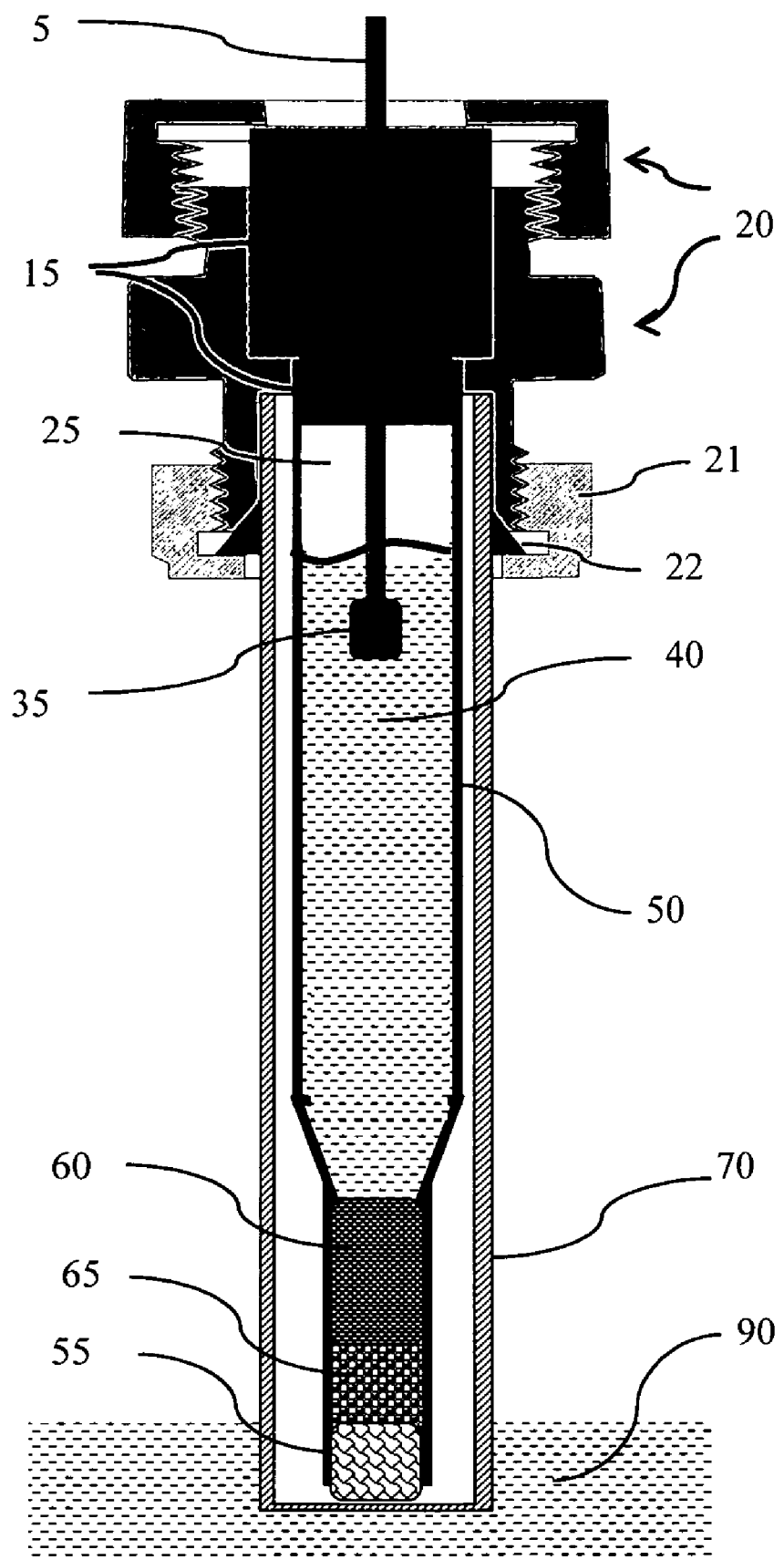

REFERENCE NUMBERS OF DRAWINGS 5 metal conductor connected to reference material (see 35)
6 metal conductor connected to reference material for pH electrode (see 36)
15 seals for reference electrode
16 seals for pH electrode
20 compression fitting
21 nut
22 seal for connection to a metal tubing (see 70)
23 thread for mounting electrode to a pressurized system
25 gas space (usually air)
35 reference material (usually Ag/AgCl)
36 internal reference material for pH electrode
40 internal electrolyte for reference electrode (usually KCl solution)
41 internal electrolyte for pH electrode
50 internal electrolyte-housing tube, usually made of heat shrink polytetrafluoroethylene (PTFE) tube
51 thin tubes or rods
54 liquid junction plug
55 outer liquid junction plug that is stable in external liquid (see 90)
60 inner liquid junction plug that has smaller and more uniform pores to restrain the outflow of the internal electrolyte (see 40)
65 sand powder or fiber
70 tubing as electrode body that facilitates installation of electrode to a pressurized system
80 internal electrolyte-housing tube of a pH electrode
81 glass bulb of a pH electrode
90 external liquid in which the electrode is used (immersed)

DETAILED DESCRIPTIONS OF THE INVENTION

Double Liquid Junction Plugs

FIG. 1 shows an improved reference electrode for high temperature applications. The reference material (35) and the internal electrolyte (40) of the reference electrode are inside the internal electrolyte-housing tube (50). The electrical lead (5) that is connected to the reference material (35) and the internal electrolyte (40) is sealed inside the internal electrolyte-housing tube with the seals (15) the compression fitting (20). The compression fitting has a nut (21) and a metal seal (22) that are used to assemble the electrode to a metal tubing (70) that facilitates the mounting of the electrode to a high pressure system that contains the external liquid (90) in which the reference electrode is used. When the electrode is assembled, a small amount of air is usually trapped inside the internal electrolyte-housing tube at the top and forms an air space (25).

In addition, there are two liquid junction plugs—the outer plug (55) and the inner plug (60)—in the improved reference electrode. The main function of the outer plug (55) is to prevent the direct contact between the inner plug and the external liquid (90) that is usually too chemically aggressive at high temperatures for most well-characterized reference liquid junction plugs. The main function of the inner plug (60) is to regulate the rate of the outflow of the internal liquid electrolyte (40), in the same way as the liquid junction plug in a regular low temperature reference electrode. Because the inner plug does not directly contact with the harsh external liquid (90), it can be selected from many of the liquid junction plugs that are commonly used in regular low temperature reference electrodes and are known to have excellent characteristics required for a reference electrode liquid junction plug, as long as it is thermally stable at the temperature of interest. One important characteristic is the porosity that restrains the outflow of the electrode and determines the liquid junction impedance (<10 kOhm). In contrast, the outer plug can be made of the materials that are highly resistant to the thermal, chemical and mechanical attacks by the harsh high temperature external liquid, but do not need to have the well-characterized porosity as required for a reference electrode liquid junction plug. This double plug design greatly reduced the difficulties in finding a material that would have the right porosity as a reference electrode liquid junction plug and the excellent thermal, chemical and mechanical stability in the harsh external liquid at high temperatures. The inventors have successfully used the tip section of a commercial reference electrode (cut off from the body of the electrode) as the inner plug. This tip section had a ceramic plug (approximately 1 mm in diameter) inside a glass casing (approximately 4 mm in outside diameter), with a total length of about 4 mm. (The commercial reference electrode was supplied by Broadley-James Corp., Irvine, Calif., USA). Detailed information for the type of glass and type of ceramic plug is not available from the supplier of the commercial reference electrode.

Because the main function of the outer plug (55) is to separate the inner plug (60) from the harsh external liquid (90), the inventors have successfully used the magnesia partially stabilized zirconia rod (TTZ) manufactured by CoorsTek, Inc. (Golden, Colo., USA). The TTZ rod was 15 mm long and had a 1-mm-diameter hole (in the center) that was filled with a zirconia fiber manufactured by Zircar Zirconia, Inc. (Florida, New York, USA). The zirconia fiber inside the TTZ rod is highly porous and acted as the ionic conducting path for the reference electrode. Because the zirconia fiber is highly porous, the zirconia fiber-filled TTZ rod cannot be used alone as the liquid junction plug because the outflow rate for the internal electrolyte was too high (>1 mL/day when tested at room temperature).

Zirconia powder (sand, can also be a ceramic fiber) (65) was packed between the inner plug (60) and the outer plug (55) to prevent the formation of gas (usually air) bubbles that may electrically isolate the reference material (35) from the external liquid (90).

Even though the outer plug (55) formed by the zirconia fiber and the bored TTZ rod and the zirconia powder (65) allowed the harsh external liquid to indirectly contact the inner plug, the outer plug effectively protected the inner ceramic plug and the glass casing—which is known to be unstable in high pH (>10) water at elevated temperatures (>100° C.)—from being dissolved by the external liquid. This is because the external liquid could only reach the inner plug by diffusion through the outer plug (55) and the zirconia powder (65) and the species dissolved from the inner plug had to diffuse out to reach the external liquid. The dissolution rate for the inner plug (ceramic and glass casing) was negligibly low because of the low mass-transfer rates. This low dissolution rate had been proven by an experiment in which the reference electrode (as shown in FIG. 1) was exposed to a pH 10 (measured at room temperature) NaOH solution at 232° C. for three months. The inner ceramic plug and the glass casing were found intact after the three-month exposure in the pH 10 NaOH solution at 232° C. The inventors' prior experience with Pyrex glass in similar solution shows that the glass (no matter what type of glass it is, because silica is the main component) would be dissolved in the NaOH solution at 232° C.

Figure 2:
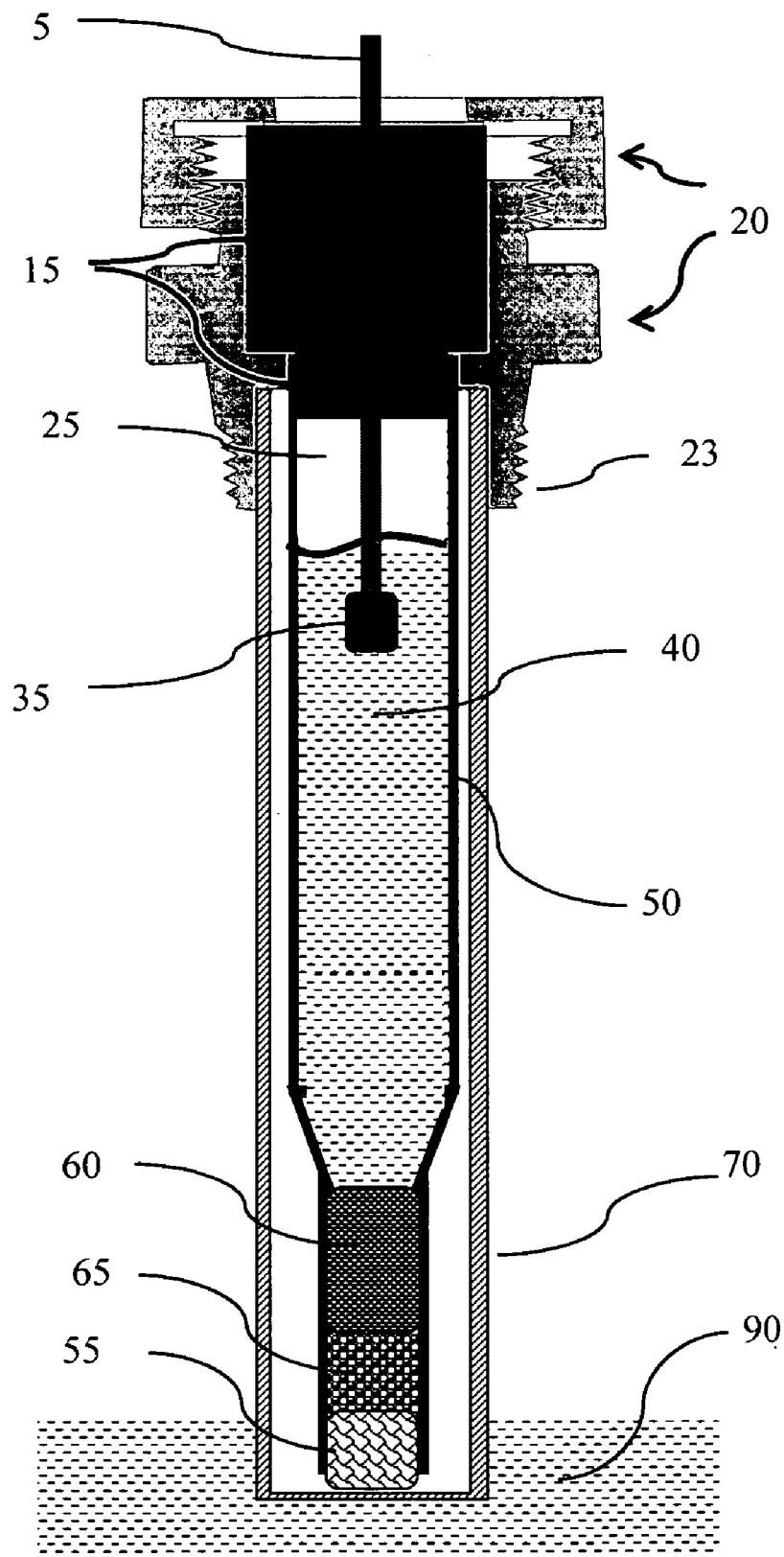

FIG. 2 shows a slight variation of the improved reference electrode in which the compression fitting (20) has a thread (23) for mounting to high pressure systems.

Method to Prevent Bubble Formation in a Liquid-Filled Tube

As shown in FIGS. 1 and 2, the air space (25) is present at the upper section of the reference electrode. When the electrode is positioned upside down or even horizontally, the air in the air space may travel to the other side of the electrode (the tip side of the electrode). Because the internal electrolyte-housing tube is usually thin (<10 mm inside diameter), the air traveled to the tip end of the electrode often forms air bubbles and the air bubbles sometimes stay near the electrode tip or are trapped somewhere between the reference material (35) and the tip of the electrode due to the surface tension. Such bubbles often cause an electrical isolation between the reference material (35) and external liquid (90) and make the reference electrode useless. Oftentimes, these bubbles cannot be removed even by shaking the reference electrode. Porous materials, such as glass fiber (see S. H. Oh, C. B. Bahn, and I. S. Hwang, "Evaluation of Thermal Liquid Junction Potential of Water-Filled External Ag/AgCl Reference Electrodes," *Journal of The Electrochemical Society*, Vol. 150, page E321-E328, 2003) and zirconia sand (see A. K. Agrawal and R. W. Staele, "A Silver-Silver Chloride Reference Electrode for the High Temperature and High Pressure Electrochemistry," *Corrosion*, Vol. 33, page 418-419, 1977), were often used inside the internal electrolyte-housing tube to avoid such gas bubbles. These porous materials maintain the electrical continuity between the reference material (35) and the external liquid (90) by capillary effect that causes the liquid to be sunken into the pores of the fiber or sand.

Figure 3:
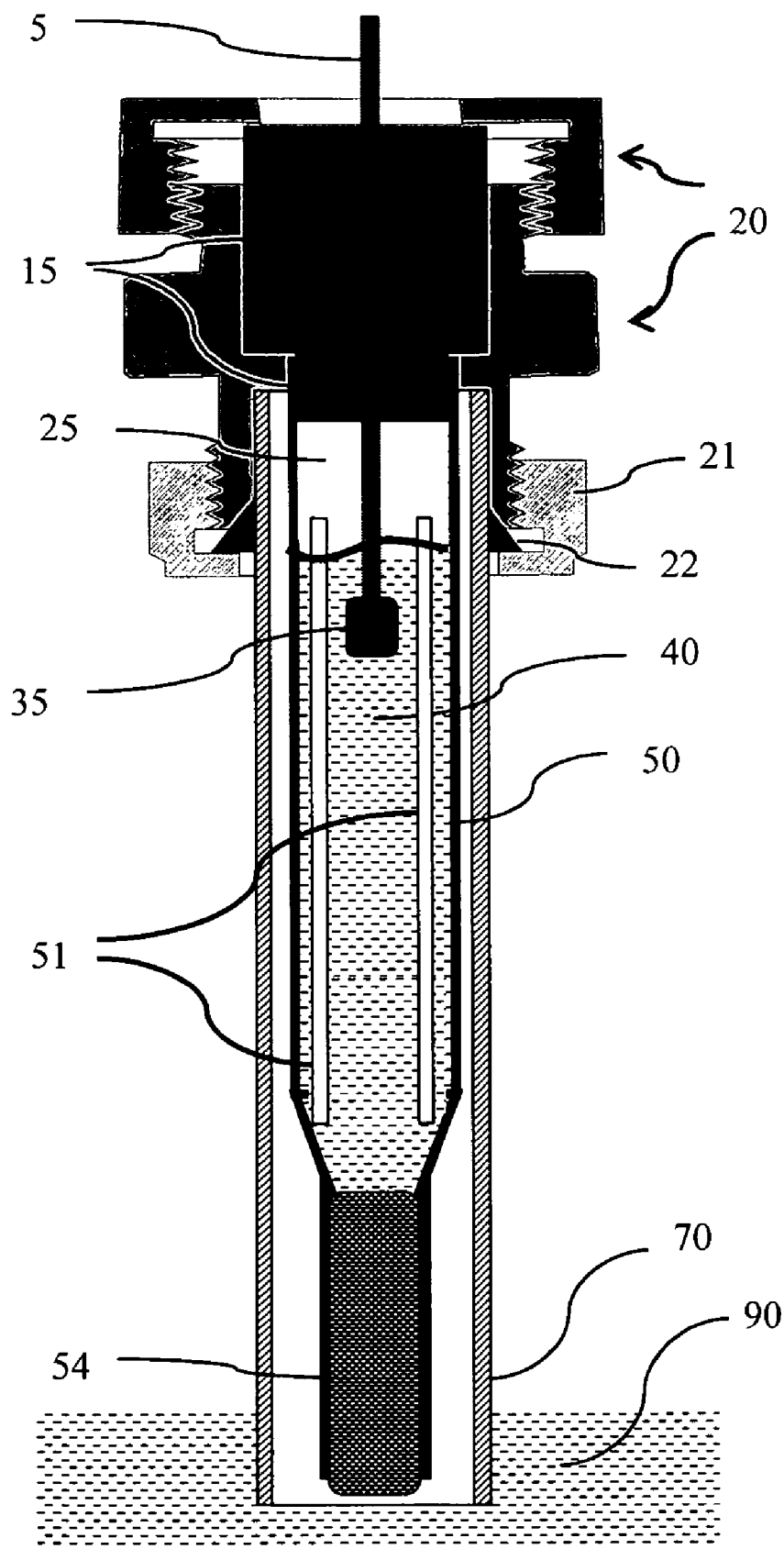
FIG. 3 illustrates a typical high pressure, high temperature reference electrode that has two thin tubes inside the internal electrolyte-housing tube to eliminate gas bubbles in the internal electrolyte.

FIG. 3 shows the new design of the reference electrode in which two pieces of thin and solid (approximately 1 mm outside diameter) polytetrafluoroethylene (PTFE) tubing (51) was inserted inside the internal electrolyte-housing tube of a normal high temperature reference electrode that has one liquid junction plug (54). Unlike the glass fiber or cotton wick, the two pieces of solid tubing are not porous and they cannot be soaked by the liquid. But the solid thin tubes break the surface tension of the air bubbles and cause the bubbles to travel to the upper location when the reference electrode is tilted or vertically placed. Thin glass rods or metal wires (stainless steel wire or silver wire) had also been tried and they were found to have similar effect of causing the bubbles to travel upward. Unlike the glass and cotton wool, which are hard to handle (e.g., to put into a long tube) and difficult to clean, the thin PTFE tubes (or thin glass rods) are easy to use and easy to clean and provide the unanticipated benefit of maintaining the continuity between the reference material (35) and the external liquid (90).

Figure 4:
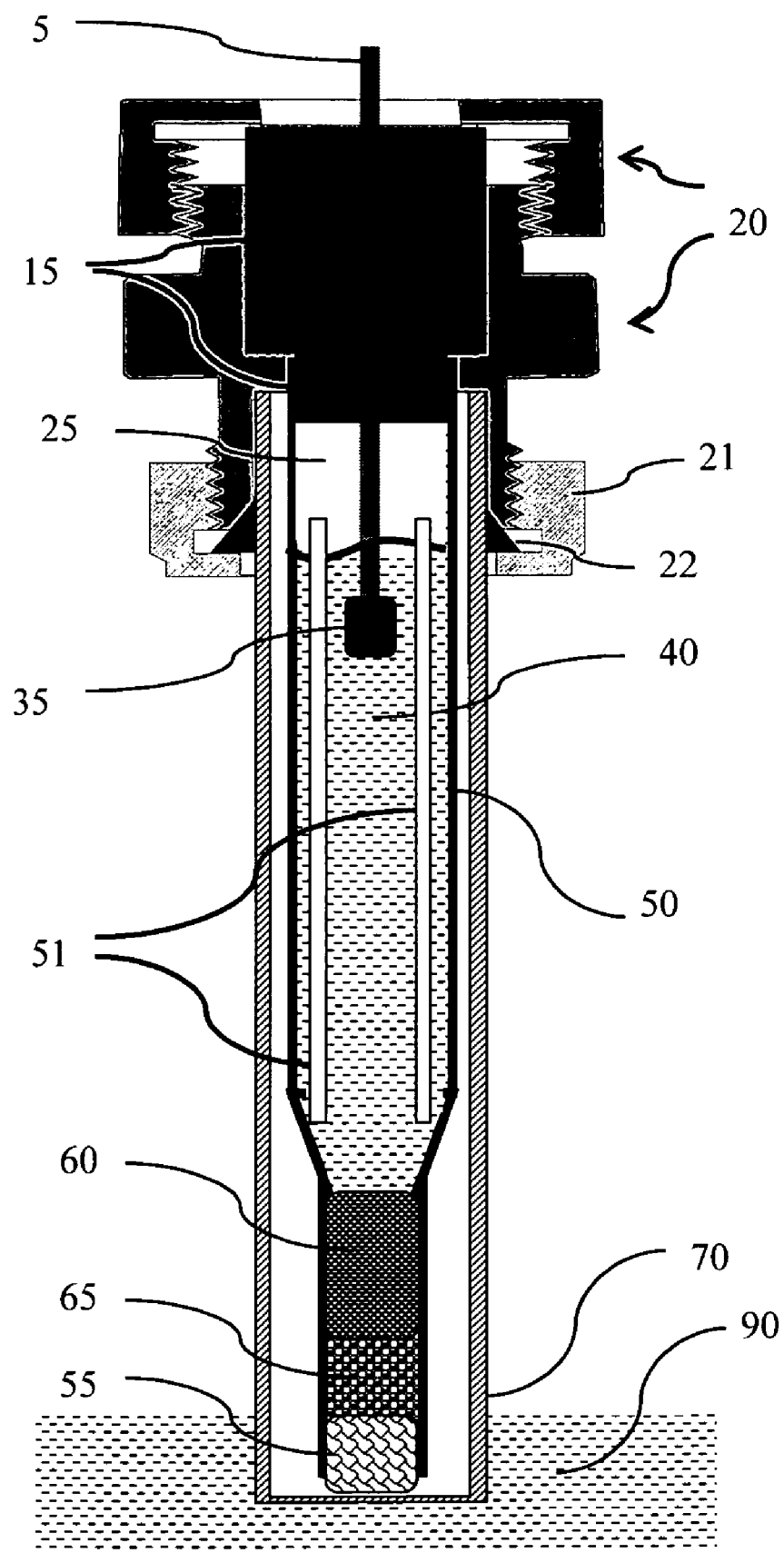
FIG. 4 illustrates a typical high pressure reference electrode that has two liquid junction plugs and sand powder in between, and two thin tubes inside the internal electrolyte-housing tube to eliminate gas bubbles in the internal electrolyte.
Figure 5:
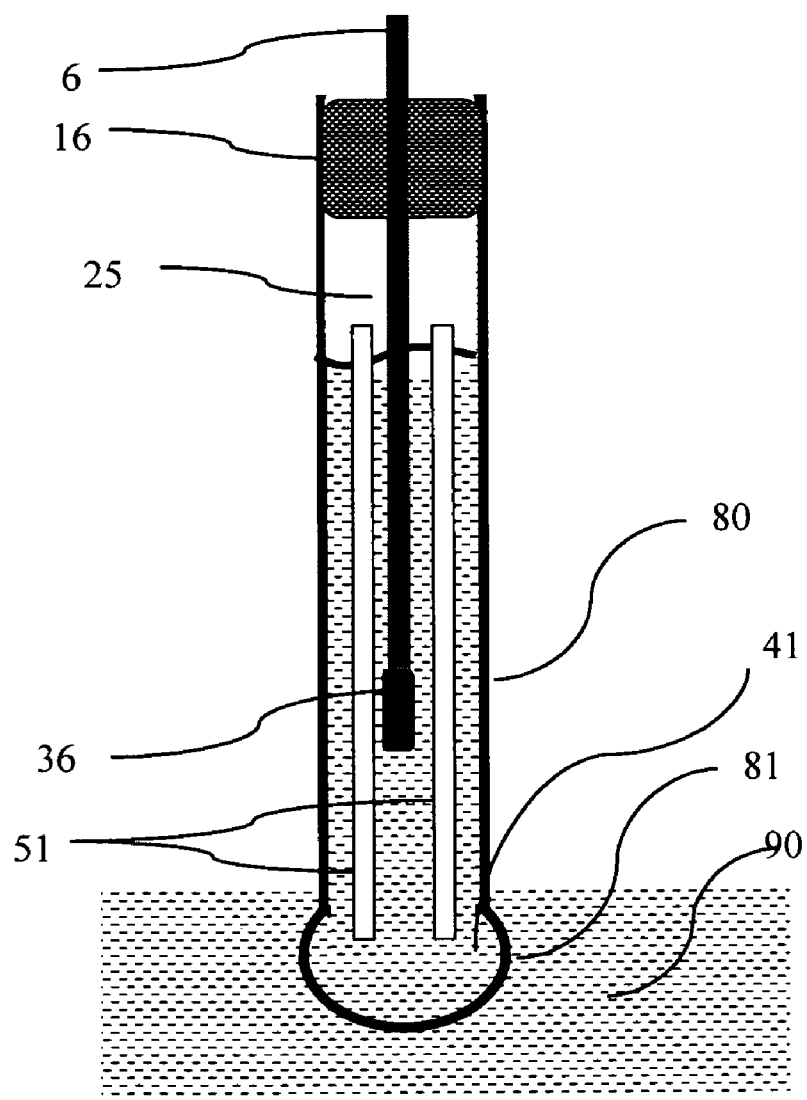
FIG. 5 illustrates a typical pH electrode that has two thin tubes inside the internal electrolyte-housing tube to eliminate gas bubbles in the internal electrolyte.

FIG. 4 shows that the thin tube pieces were also used in the improved reference electrode, as shown in FIGS. 1 and 2, in which double liquid junction plugs were used. FIG. 5 shows that the two thin tubes/rods (51) were also used in a pH electrode to void the formation of gas bubbles between the reference material (36) and the glass bubble (81) of the pH electrode.

OTHER EMBODIMENTS

Although commercial reference electrode ceramic plugs were used as the inner plug in the tests conducted by the inventors, other porous materials that have uniformly distributed micropores and provide the desired outflow rate for the internal electrolyte and low junction impedance can also be used as the inner plugs. Such porous materials may include, but not be limited to, porous glass, porous ceramic, porous polymers, porous minerals, and ceramic or glass fibers and wools, as long as these materials are thermally stable at the intended use temperature. The outer plug is not limited to the magnesium stabilized zirconia. It can be any material that is chemically, thermally, and mechanically stable at the intended use temperature and the environment, provided it allows the external liquid to have electrical (ionic) contact with the inner plug. The zirconia sand packing between the inner plug and the outer plug can also be replaced by any material that enables the electrical continuity between the inner plug and the outer plug by capillary action. Such packing may also be omitted if a mechanism is designed into the inner and the outer plugs that ensures a reliable electrical contact between the inner plug and the outer plugs when the reference electrode is immersed in a solution.

The method used to prevent the formation of the gas bubbles inside the internal electrolyte-housing tubes using thin tubes or thin rods may also be used for other systems containing a liquid-filled tube.

Although the present invention has been described in detail, it should be understood that various changes, substitutions, and alterations can be made hereto, without departing from the spirit and scope of the invention as defined by the appended claims.

The invention claimed is:

1. A high-pressure reference electrode for high-temperature applications, comprising:
   (a) a tube for housing an internal reference electrolyte and a metal conductor connected to a reference material at the bottom;
   (b) seals at the top of the tube that seal the internal reference electrolyte and the reference material inside the tube and allow the metal conductor to penetrate for electrical connection;
   (c) an outer plug that is sealed to the lower end of the tube and is exposed directly to a harsh high-temperature external liquid and has sufficient ionic conductivity
   (d) an inner plug that is for regulating the outflow of the internal reference electrolyte, but is less resistant to the harsh high-temperature external liquid than the outer plug, and is sealed to the inside wall of the tube above the outer plug so that the inner plug is in direct contact with the internal reference electrolyte, but separated from the external liquid by the outer plug;
   wherein the inner plug provides the function of restraining the outflow of the internal reference electrolyte and the outer plug provides the function of preventing the inner plug from directly contacting the external liquid and protecting the inner plug from being chemically or mechanically attacked by the external liquid so that the inner plug has a low degradation rate when the reference electrode is exposed to the external liquid.

2. The reference electrode of claim 1, wherein a porous packing is used between the inner plug and the outer plug to ensure the electrical continuity between the inner plug and the outer plug when the reference electrode is immersed in the external liquid.

3. The reference electrode of claim 2, wherein the porous packing is zirconia powder.

4. The reference electrode of claim 2, wherein the porous packing is zirconia fiber.

5. The reference electrode of claim 1, wherein the outer plug is zirconia-containing ceramic.

6. The reference electrode of claim 1, wherein the outer plug is a porous zirconia.

* * * * *